United States Patent [19]
Duflot et al.

[11] Patent Number: 5,856,469
[45] Date of Patent: Jan. 5, 1999

[54] METHOD FOR PRODUCING PALATINITOL

[75] Inventors: Pierrick Duflot, Lacouture; Catherine Fouache, Sailly Labourse, both of France

[73] Assignee: Roquette Freres, France

[21] Appl. No.: 860,722

[22] PCT Filed: Nov. 14, 1996

[86] PCT No.: PCT/FR96/01798

§ 371 Date: Sep. 12, 1997

§ 102(e) Date: Sep. 12, 1997

[87] PCT Pub. No.: WO97/19094

PCT Pub. Date: May 29, 1997

[30] Foreign Application Priority Data

Nov. 17, 1995 [FR] France .................................. 95 13647

[51] Int. Cl.$^6$ .............................. C07H 1/00; C07C 29/00; C07C 27/00
[52] U.S. Cl. .......................... 536/124; 536/1.11; 536/125; 568/863; 568/862; 568/861
[58] Field of Search .................................. 536/124, 1.11; 568/863, 861, 862

[56] References Cited

U.S. PATENT DOCUMENTS 4,684,720 8/1987 Darsow et al. ........................... 536/124
5,644,044 7/1997 Darsow et al. ........................... 536/18.5

FOREIGN PATENT DOCUMENTS 2515186 4/1983 France .
3403973 8/1985 Germany .
63-96195 4/1988 Japan .
63-162698 7/1988 Japan .

OTHER PUBLICATIONS

Database WPI, Section Ch, Week 9225 Derwent Publications Ltd., London, GB; Class B03, AN 92–203078 XP002010687 & JP 04 121 198 A, Abstract.

"Alternative Sweeteners" by Lyn O'Brien Nabors, Chap. 11, pp. 217–244, 1986.

*Primary Examiner*—Douglas W. Robinson
*Assistant Examiner*—Everett White
*Attorney, Agent, or Firm*—Henderson & Sturm

[57] ABSTRACT

"A process for the preparation of palatinitol, wherein in a first stage, the epimerization of isomaltose is carried out under conditions which allow a mixture of α-D-glucopyranosyl-(1→6)-D-mannose and isomaltose to be obtained, in a second stage, the epimerized mixture is depleted of isomaltose so as to obtain a new mixture containing a roughly equimolecular proportion of α-D-glucopyranosyl-(1→6)-D-mannose and isomaltose, and in a third stage, catalytic hydrogenation is carried out on this roughly eqimolar mixture".

5 Claims, No Drawings

METHOD FOR PRODUCING PALATINITOL

This application is a 371 of PCT/FR96/01798, filed Nov. 14, 1996.

The present invention relates to a new process for producing palatinitol.

More particularly it relates to a production process for palatinitol starting from isomaltose or α-D-glucopyranosyl-(1→6)-D-glucose.

BACKGROUND OF THE INVENTION

Palatinitol is a sweetening agent of low caloric mass and low cariogenicity which up to now is obtained by catalytic Hydrogenation at neutral pH of isomaltulose or α-D-glucopyranosyl-(1→6)-D-fructose.

Isomaltulose is itself obtained by enzymatic isomerization, using a saccharose glysosyl transferase, saccharose or α-D-glucopyranosyl-(1→2)-β-D-fructofuranoside.

Therefore, it is saccharose which constitutes the raw material for obtaining palatinitol, a mixture in roughly equimolecular proportions, of α-D-glucopyranosyl-(1→6)-D-sorbitol (GPS or isomaltitol) and α-D-glucopyranosyl-(1→6)-D-mannitol (GPM).

Palatinitrol, which is also called isomalt, is in particular marketed by the Company Süddeutsche Zucker AG under the name Palatinit®.

Among other documents which concern the obtaining and properties of palatinitol the following work can be referred to: "Alternative Sweeteners" published in 1986 by LYN O'BRIEN NABORS, chapter 11, pages 217 to 244.

Concerned to develop a process which allows palatinitol to be obtained from a raw material other than saccharose, the Applicant Company has noticed that this goal could be achieved by a process using isomaltose or α-D-glucopyranosyl-(1→6)-D-glucose.

In accordance with the present invention, palatinitol is obtained thanks to a process characterized in that
  in a first stage, the epimerization of isomaltose is carried out under conditions which allow a mixture of α-D-glucopyranosyl-(1→6)-D-mannose and isomaltose to be obtained,
  in a second stage, the epimerized mixture is depleted of isomaltose so as to obtain a mixture containing a roughly equimolecular proportion of α-D-glucopyranosyl-(1→6)-D-mannose and isomaltose,
  in a third stage, catalytic hydrogenation is carried out on this mixture.

If it is reasonable to imagine that palatinitol may be obtained from saccharose, the person skilled in the art could in no way expect that this same palatinitol might be obtained from isomaltose which is obtained from glucose and thus from diverse and various starches.

In fact, in the first case, saccharose, the structural formula of which includes a fructose unit, will produce, in a known fashion by enzymatic isomerization, the corresponding ketose i.e. isomaltulose.

And it is known to the person skilled in the art that the hydrogenation of such a ketose leads to the formation of the two corresponding itols in approximately equimolecular proportions. Therefore, the fact that the formula of saccharose is related to that of palatinitol allows the result to be anticipated.

However, the process according to the invention does not implement a starting product whose formula is related to that of the sought palatinitol. In fact, isomaltose as well as glucose and starch have a structure which does not contain a fructose unit and is therefore far from being related to that of palatinitol.

BRIEF SUMMARY OF THE INVENTION

The process according to the invention therefore allows freedom from the requirement to use saccharose as raw material for the production of palatinitol since isomaltose can be easily obtained from glucose and therefore from diverse and varied starches, whether they originate from cereals or tubers.

A process for obtaining isomaltose from glucose or a corn syrup is described, for example, in the French Patent Application 2,515,186.

DETAILED DESCRIPTION OF THE INVENTION

In the process according to the invention, it is preferred to use crystallized isomaltose, although syrups which are very rich in isomaltose are also suitable if one accepts that maltitol or isomaltotriitol may be present in the palatinitol. The two last-named compounds originate from the hydrogenation of maltose or isomaltotriose which represent the main impurities in syrups which are very rich in isomaltose.

In the process according to the invention, the epimerization of isomaltose can be carried out as described in the Japanese Patent Application 63-162698 using a metallic salt and an amine but it is preferably carried out in the manner described in the Japanese Patent Application 63-96195 and which consists of reacting an aqueous solution of isomaltose, at a pH comprised between 2.5 and 4, in the presence of molybdic anhydride or hexavalent molybdenum salts, at a temperature comprised between 90° C. and 140° C.

Preferably, ammonium molybdate is used in a proportion of approximately 0.1 to 1.5% by weight relative to the isomaltose.

More preferably, the epimerization of isomaltose is carried out in the form of an aqueous sweetened solution containing 10 to 70% isomaltose.

The epimerization conditions are adjusted (essentially the catalyst content, the duration of epimerization and the reaction temperature) so as to obtain a mixture of isomaltose and α-D-glucopyranosyl-(1→6)-D-mannose, containing 10 to 40% of the latter compound. It is not economical to treat mixtures containing less than 10% of this compound, and mixtures containing more than 40% of it contain too many impurities which form under the extreme conditions of epimerization.

It is preferred to operate under conditions which allow 20 to 35% of α-D-glucopyranosyl-(1→6)-D-mannose to be obtained and yet more preferably from 25 to 35% of this compound.

The mixture obtained in this way is then demineralized on ion exchange resins in order to remove the salts which have been used as the catalyst.

In the process according to the invention depleting the epimerized mixture of isomaltose can be carried out in different ways.

For example, the epimerized mixture can be subjected to the action of an amylglucosidase which has the effect of hydrolyzing the isomaltose into two glucose molecules. This glucose can then be eliminated in the form of gluconic acid by the action of a glucose oxidase which converts this glucose into gluconic acid which is eliminated by ion exchange on anionic resins. This glucose can also be consumed using yeasts or bacteria.

However, it is preferred to deplete the epimerized mixture of isomaltose by chromatographic route.

As a rule, when a chromatographic stage is used to achieve the separation of two components from a binary mixture, the chromatography is carried out in such a way that the two components are separated in the most complete fashion possible, i.e. in order to obtain a fraction A which only contains very little of compound B and a fraction B which only contains very little of compound A.

In the process according to the invention, the depletion of the epimerized mixture in isomaltose is, on the contrary, carried out in such a manner as to obtain a fraction containing a roughly equimolecular proportion of isomaltose and α-D-glucopyranosyl-(1→6)-D-mannose, the other fraction being constituted by very pure isomaltose. By roughly equimolecular is meant from 40 to 60% and more preferably from 45 to 55% of one of the two compounds relative to the total mass of the two compounds. This way of proceeding has the advantage of directly obtaining a mixture which after hydrogenation will provide the two components of palatinitol, namely isomaltitol and GPM in roughly equimolecular proportions, without having to resort to remixing pure fractions.

Advantageously, the isomaltose, the content of which is routinely comprised between 85% and 95%, is recycled, the remainder being above all constituted by α-D-glucopyranosyl-(1→6)-D-mannose, at the epimerization stage.

This way of proceeding allows yields close to 100% of palatinitol to be obtained relative to the isomaltose used and therefore constitutes the preferred method of implementing the process according to the present invention.

This chromatographic stage is carried out very easily on an industrial scale by application of the epimerized mixture on a column loaded with cation exchange resins of a cross-linked sulphonated polystyrene-divinylbenzene type. These resins, in order to be suitable for the chromatography must have a very fine and very homogeneous granulometry, advantageously comprised between 150 and 400 microns, and for their use, are permuted in alkaline or alkaline-earth form. The mixture applied to the column is then fractionated by elution with water from the resin.

Surprisingly, it was noted that whilst the isomaltose and the α-D-glucopyranosyl-(1→6)-D-mannose have similar structures and strictly identical molecular weights, the migration of the isomaltose in the resin is much faster.

From here it is sufficient to extract from the resin at the start of the elution cycle the strictly necessary quantity of isomaltose to produce in a roughly equimolecular proportion the components of the mixture to be subjected to chromatography.

This chromatography stage can be carried out in a discontinuous fashion on a single column of resin or on several columns operating in parallel, but it is more advantageously carried out on multicolumn systems connected in a loop, working on the principle of a simulated fluidized bed. These systems have the advantage of obtaining better performances from the resin and of working continuously.

In a general fashion, to obtain the best performances from chromatographic resins it is preferred to carry out this chromatography at a temperature comprised between 60° and 90° C. It is preferred to chromatograph epimerized mixtures having a dry matter content comprised between 7 and 70%, preferably comprised between 10 and 50%. As has already been mentioned above, the fraction excluded at the start of the elution cycle, which is rich in isomaltose, is advantageously recycled at the epimerization stage. The adsorbed fraction representing the end of the elution cycle and containing the remainder of the isomaltose and the α-D-glucopyranosyl-(1→6)-D-mannose in roughly stoichiometric proportions, is then concentrated to a dry matter content of approximately 30% to 60% with a view to its catalytic hydrogenation under economical conditions.

Such a hydrogenation is carried out in a manner known per se, continuous or discontinuous, under a hydrogen pressure of 30 to 200 bars, at a temperature of 80° to 150° C. in the presence of a catalyst based on nickel or ruthenium and at a pH close to neutral. Hydrogenation carried out at a pH of less than 4.0 will result in partial hydrolysis of the isomaltose into glucose and the α-D-glucopyranosyl-(1→6)-D-mannose into glucose and mannose with the appearance of sorbitol and mannitol in the palatinitol. Hydrogenation at a pH higher than 9 will result in changing the stoichiometry between the two components of palatinitol.

In a general fashion, the hydrogenation is carried out until the content of the reducing sugars, measured by the Bertrand method, becomes lower than 1% and preferably, lower than 0.5%.

After the hydrogenation stage, the syrups obtained are purified to remove the catalyst by filtration then demineralization on ion exchange resins.

The hydrogenated and purified syrups are then concentrated, crystallized and dried to produce a commercial powder of palatinitol which is in fact a mixture of crystals of anhydrous isomaltitol and GPM dihydrate in roughly equimolecular proportions.

The present invention is illustrated by the following example which is non-limitative, the Applicant only having the purpose of explaining what appears to him to be one of the best means of implementing the process of his invention.

EXAMPLE

First stage 4 grams of crystallized isomaltose as well as 16 mg of ammonium molybdate $(NH_4)_6 Mo_7 O_{24}$, i.e 0.4% by weight relative to the isomaltose are put in solution in 36 grams of water, then the pH of this solution is adjusted to 3.5 using hydrochloric acid.

This solution is then heated to 130° C. for 15 minutes.

After cooling down, this solution is demineralized on a mixed bed of strong cationic and anionic resins which produces an epimerized mixture, the resistivity of which is greater than $2.10^6$ ohms.cm.

HPLC chromatography of this epimerized mixture reveals the presence of 35% of α-D-glucopyranosyl-(1→6)-D-mannose and 65% of isomaltose. The presence of glucose and mannose are also observed, although in trace amounts.

Second stage 340 cm³ of the resin marketed under the tradename PCR 532 by the company PUROLITE is introduced into a double jacket glass column thermostatically controlled at 85° C., 2 meters high with an internal diameter of 15 mm. This resin has the following characteristics:

skeleton: cross-linked sulphonated polystyrene-divinylbenzene cross-linking ratio: 5% particle size: 180 to 280 microns ionic form for use: $Ca^{++}$ 2.5 cm³ of epimerized mixture with 10% dry matter is introduced at the top of the column, and then percolates through this resin, being eluted with water at a flow rate of 210 cm³/hour.

After having eluted 140 cm³ of water, a fraction of isomaltose starts to collect representing 27 cm³.

This fraction of isomaltose shows under analysis by gas chromatography a content of 89% isomaltose and 11% α-D-glucopyranosyl-(1→6)-D-mannose.

Immediately following this fraction of isomaltose, a fraction of 64 cm³ is collected constituted by a mixture depleted, in isomaltose analysis by gas chromatography of which reveals a content of 47% isomaltose and 52% α-D-glucopyranosyl-(1→6)-D-mannose. This analysis also reveals traces of glucose and mannose.

This stage is carried out 15 times in order to obtain a fraction of isomaltose with an average content of 90% and a fraction of a mixture of approximately equal parts of isomaltose and α-D-glucopyranosyl-(1→6)-D-mannose.

The excluded chromatographic fraction, which is rich in isomaltose was concentrated under vacuum until a dry matter content of 10% was obtained.

Another 0.4% of ammonium molybdate relative to the estimated dry content of the chromatographic fraction is added and the reaction medium is again subjected to epimerization under the conditions described with respect to the epimerization stage No. 1. Once again 35% of α-D-glucopyranosyl-(1→6)-D-mannose was obtained.

The adsorbed chromatographic fraction, which contains as much isomaltose as α-D-glucopyranosyl-(1→6)-D-mannose was concentrated to a dry matter content of 40% with a view to subjecting it to hydrogenation.

This fraction, not including the fraction of isomaltose recycled at the epimerization stage, represents 64% of the dry matter subjected to chromatographic fractionation.

Third stage

This adsorbed fraction is introduced into a hydrogenation reactor in the presence of 5% by weight of sugars and of Raney nickel. After placing the apparatus under a hydrogen pressure of 50 bars which is maintained throughout the duration of hydrogenation, the contents of the reactor are heated to the temperature of 125° C. The pH of the reaction medium is maintained at 8.0 throughout this hydrogenation using a solution of sodium bicarbonate. Hydrogenation is stopped after 8 hours, when the content of reducing sugars in the reaction medium, measured by the Bertrand method, has become less than 0.1%.

The contents of the hydrogenation reactor are then filtered to remove the catalyst then the syrup is demineralized on a mixed bed of resins, as in the first stage. In this way a perfectly clear and colourless syrup is obtained, the composition of which using analysis by gas chromatography proves to be as follows:

isomaltitol: 49.1%

GPM: 49.4%

This syrup is then concentrated so as to bring its two components to the crystallized state which are then dried in order to obtain a white and non-hygroscopic powder of palatinitol titrating 5.1% dampness.

We claim:

1. Process for the preparation of palatinitol, wherein:
   in a first stage, the epimerization of isomaltose is carried out under conditions which allow a mixture of α-D-glucopyranosyl-(1→6)-D-mannose and isomaltose to be obtained,
   in a second stage, the epimerized mixture is depleted of isomaltose so as to obtain a new mixture containing a roughly equimolecular proportion of α-D-glucopyranosyl-(1→6)-D-mannose and isomaltose,
   in a third stage, catalytic hydrogenation is carried out on this roughly equimolecular mixture.

2. Process according to claim 1, wherein the epimerization is carried out in the presence of a hexavalent molybdenum salt.

3. Process according to claim 1, wherein depleting the epimerized mixture of isomaltose is carried out by chromatography on cationic resins in alkaline or alkaline-earth form.

4. Process according to claim 3, wherein the cationic resins are in calcium form.

5. Process according to one or other of claims 3 and 4, wherein the fraction of isomaltose excluded from the chromatographic stage is recycled at the epimerization stage.

* * * * *